(12) United States Patent
Kaneko et al.

(10) Patent No.: US 10,034,500 B2
(45) Date of Patent: Jul. 31, 2018

(54) GARMENT

(71) Applicant: Seiko Instruments Inc., Chiba-shi, Chiba (JP)

(72) Inventors: Takahiro Kaneko, Chiba (JP); Dai Terasawa, Chiba (JP); Hideki Okuda, Chiba (JP); Teruo Kato, Chiba (JP)

(73) Assignee: SEIKO INSTRUMENTS INC., Chiba (JP)

(*) Notice: Subject to any disclaimer, the term of this patent is extended or adjusted under 35 U.S.C. 154(b) by 898 days.

(21) Appl. No.: 14/518,406

(22) Filed: Oct. 20, 2014

(65) Prior Publication Data

US 2015/0119675 A1 Apr. 30, 2015

(30) Foreign Application Priority Data

Oct. 25, 2013 (JP) ................... 2013-222229

(51) Int. Cl.
| | |
|---|---|
| *A61B 5/0408* | (2006.01) |
| *A41D 13/12* | (2006.01) |
| *A61B 5/00* | (2006.01) |
| *A61B 5/024* | (2006.01) |
| *A61B 5/0245* | (2006.01) |
| *A41D 27/20* | (2006.01) |

(52) U.S. Cl.
CPC ........ *A41D 13/1281* (2013.01); *A61B 5/0245* (2013.01); *A61B 5/02438* (2013.01); *A61B 5/0408* (2013.01); *A61B 5/6804* (2013.01); *A61B 5/6805* (2013.01); *A41D 27/205* (2013.01)

(58) Field of Classification Search
CPC ..... A61B 5/6804; A61B 5/6805; A61B 5/065; A61B 5/02438; A61B 5/0245; A61N 1/0484; A63B 21/065; A41D 13/1281; A41D 27/205
USPC .................................. 600/388–390
See application file for complete search history.

(56) References Cited

U.S. PATENT DOCUMENTS

| | | | |
|---|---|---|---|
| 6,687,523 B1 * | 2/2004 | Jayaramen | A41D 13/1281 600/388 |
| 2005/0261564 A1 * | 11/2005 | Ryu | A61B 5/04085 600/388 |
| 2005/0275416 A1 * | 12/2005 | Hervieux | A41D 13/1281 324/663 |

(Continued)

FOREIGN PATENT DOCUMENTS

| | | |
|---|---|---|
| JP | 4721700 B2 | 7/2011 |
| JP | 5176202 B2 | 4/2013 |

*Primary Examiner* — Lee S Cohen
*Assistant Examiner* — Eunhwa Kim
(74) *Attorney, Agent, or Firm* — Brinks Gilson & Lione (57) ABSTRACT

Provision of a garment capable of positively holding a biological information detecting device and suppressing the reduction of product lifetime to realize improvement in productivity and reduction of costs. A garment 100A includes a garment body 101 and a device housing portion 120 provided in the garment body 101 and holding a heart rate measuring device 10 having a device body 20 and electrodes 26A and 26B contacting a biological surface so as to be attached/detached, in which the device housing portion 120 holds part of the device body 20 in a state where the electrodes 26A and 26B are exposed toward the biological surface side. The device housing portion 120 houses the device body 20 in a stretched state.

2 Claims, 11 Drawing Sheets

(56) References Cited

U.S. PATENT DOCUMENTS

| | | | |
|---|---|---|---|
| 2006/0135863 A1* | 6/2006 | Birnbaum | A61B 5/0002 600/388 |
| 2007/0209669 A1* | 9/2007 | Derchak | A24F 47/00 131/329 |
| 2011/0184270 A1* | 7/2011 | Russell | A61B 5/02055 600/388 |
| 2013/0053674 A1* | 2/2013 | Volker | A61B 5/04085 600/389 |
| 2014/0237696 A1* | 8/2014 | Carver | A41D 13/0575 2/24 |

* cited by examiner

GARMENT

RELATED APPLICATIONS

This application claims priority under 35 U.S.C. § 119 to Japanese Patent Application No. 2013-222229 filed on Oct. 25, 2013, the entire content of which is hereby incorporated by reference.

BACKGROUND OF THE INVENTION

1. Field of the Invention

The present invention relates to a garment worn by a user of a biological information detecting device.

2. Description of the Related Art

There exist biological information detecting devices detecting a biological signal by attaching a sensor electrode to a biological surface. In this kind of biological information detecting devices, there is the one which measures a heart rate from the biological surface, for example, by detecting an electrocardiographic signal generated by heartbeats by the sensor electrode. As such biological information detecting device, there is the one which includes a sensor electrode and a device body (transmission unit) transmitting an electrocardiographic signal detected by the sensor electrode to the outside. The heart rate is measured by a separate receiving unit receiving the signal transmitted from the device body.

The sensor electrode and the device body are attached to a user's body by using an annular band having elasticity such as a rubber band. The user puts on the sensor electrode and the device body so that the annular band is attached around the body. Accordingly, the sensor electrode is pressed to closely contact the biological surface, so that the electrocardiographic signal is detected.

Incidentally, it is necessary that the sensor electrode is held at a predetermined position in the body which is suitable for detecting the electrocardiographic signal during the use for positively detecting the electrocardiographic signal. Accordingly, a tightening force by the band is adjusted also during exercise and so on to prevent displacement of the sensor electrode. However, the user may feel a sense of oppression when the tightening force by the band is high due to the adjustment.

In response to the above, a structure in which a band with a sensor electrode is integrally attached to a garment is disclosed in, for example, Japanese Patent No. 4721700 (Patent Literature 1).

Moreover, a structure in which a sensor electrode is woven into a garment as part of the garment by using conductive yarn is disclosed in, for example, Japanese Patent No. 5176202 (Patent Literature 2).

As shown in Patent Literatures 1 and 2, as the sensor electrode is integrally attached to the garment, a position of the sensor electrode with respect to the body is not largely displaced when the user wears the garment on the body.

However, in the structures disclosed in Patent Literatures 1 and 2, the sensor electrode is easily deteriorated by washing the garment as the sensor electrode is integrally attached to the garment. Accordingly, there is room for improvement in extension of product lifetime.

As the sensor electrode attached to the garment, for example, by being woven into the garment, which may cause problems such as reduction in productivity and increase of manufacturing costs.

SUMMARY OF THE INVENTION

In view of the above, an object of the present invention is to provide a garment capable of positively holding the biological information detecting device and suppressing the reduction of product lifetime to realize improvement in productivity and reduction of costs.

According to an embodiment of the invention, there is provided a garment formed so that a biological information detecting device having a device body and electrode portions contacting a biological surface can be attached and detached to and from a garment body, which includes a device housing portion housing the device body in a state where the electrode portions are exposed toward the biological surface side.

According to the present invention, at least part of the device body is held by the device housing portion, and the electrode portions are in a state of being exposed toward the biological surface. Therefore, the garment is worn by the user, thereby holding the biological information detecting device in a state where the electrode portions are allowed to contact the biological surface.

As the biological information detecting device can be attached and detached to and from the device housing portion, the biological information detecting device can be detached from the garment body when the garment body is washed. Accordingly, as the garment body can be washed alone, the garment body can be changed freely and the biological information detecting device (for example, the electrode portions and so on) is not deteriorated due to the washing. Additionally, as the biological information detecting device can be held only by providing the device housing portion, improvement in productivity and reduction of costs can be realized. Accordingly, it is possible to suppress the reduction of product lifetime, to improve productivity and to reduce costs.

The device housing portion may be made of a material having stretch property, housing the device body in a stretched state.

According to the present invention, the device body can be held by the stretch property of the device housing portion.

The device housing portions may be arranged along a first direction in plane directions of the garment body to form a housing portion group.

According to the present invention, the device housing portion for holding the device body can be selected from the arranged housing portion group. As the position of the device body can be adjusted along the first direction of the garment body, the device body can be attached so as to be fitted to the body of the user. As a result, it is possible to attach the device body to an appropriate position to thereby fulfill a required function. Also, the user can attach the device body at a position comfortable for the user.

Plural housing portion groups may be arranged in a second direction perpendicular to the first direction in plane directions of the garment body, and the device housing portion of one housing portion group adjacent to another housing portion group may be positioned between device housing portions in that other housing portion group in the first direction.

According to the present invention, the device body can be positively held by plural device housing portions arranged in the second direction. The device body is allowed to be held in the device housing portion in one housing portion group adjacent to another housing portion group, thereby allowing the device body to be held between the device holding portions in that other housing portion group in the first direction. Therefore, the device body can be held in a required position.

The device body may be housed in plural device housing portions so as to bridge between the device housing portions in plural housing portion groups.

According to the present invention, the device body can be positively held by plural device holding portions.

The garment body may be worn in the upper half of a body, plural device housing portions may be arranged along a lengthwise direction, and a separation distance between the device housing portions arranged in one line and the device housing portions arranged in another line may be gradually reduced from an upper part of the garment body toward a lower part thereof.

According to the present invention, it is possible to prevent the device body from falling off from the device housing portion even when a lower part of the garment deformed so as to be stretched due to the movement of the user who wears the garment.

Plural device housing portions may be connected, and the device housing portion positioned at one end side in the plural device housing portions may be fixed to the garment body, and the device housing portion positioned in the other end side may be formed so as to be rotatable with the device housing portion positioned at one end side as an origin.

According to the present invention, the other end side is rotated with one end side as the origin in plural device housing portions connected to one another, thereby arranging the device housing portion to a different position with respect to one end side fixed to the garment body. Accordingly, the position where the device body is fixed to the garment body can be adjusted in a wider range.

The device housing portion may be provided in an obverse surface side of the garment body, and the garment body may have slits at outer sides of the device housing portion for allowing the electrode portions to be drawn out to a reverse surface side of the garment body.

According to the present invention, it is possible to allow the electrode portions to pierce to the reverse side of the garment through the slits and to contact the body surface of the user.

According to the present invention, at least part of the device body is held by the device housing portion, and the electrode portions are in a state of being exposed toward the biological surface. Accordingly, the biological information detecting device can be held in the state where the electrode portions are allowed to contact the biological surface when the garment is worn by the user.

Additionally, as the biological information detecting device can be attached and detached to and from the device housing portion, the biological information detecting device can be detached from the garment body when the garment body is washed. Accordingly, as the garment body can be washed alone, the garment body can be changed freely, and the biological information detecting device (for example, the electrode portions and so on) is not deteriorated due to the washing. Furthermore, as the biological information detecting device can be held only by providing the device housing portion, improvement in productivity as well as reduction of costs can be realized. Accordingly, it is possible to suppress the reduction of product lifetime, to improve productivity and to reduce costs.

DETAILED DESCRIPTION OF THE PREFERRED EMBODIMENTS

First Embodiment

Next, a first embodiment of the present invention will be explained with reference to the drawings.

Figure 1:
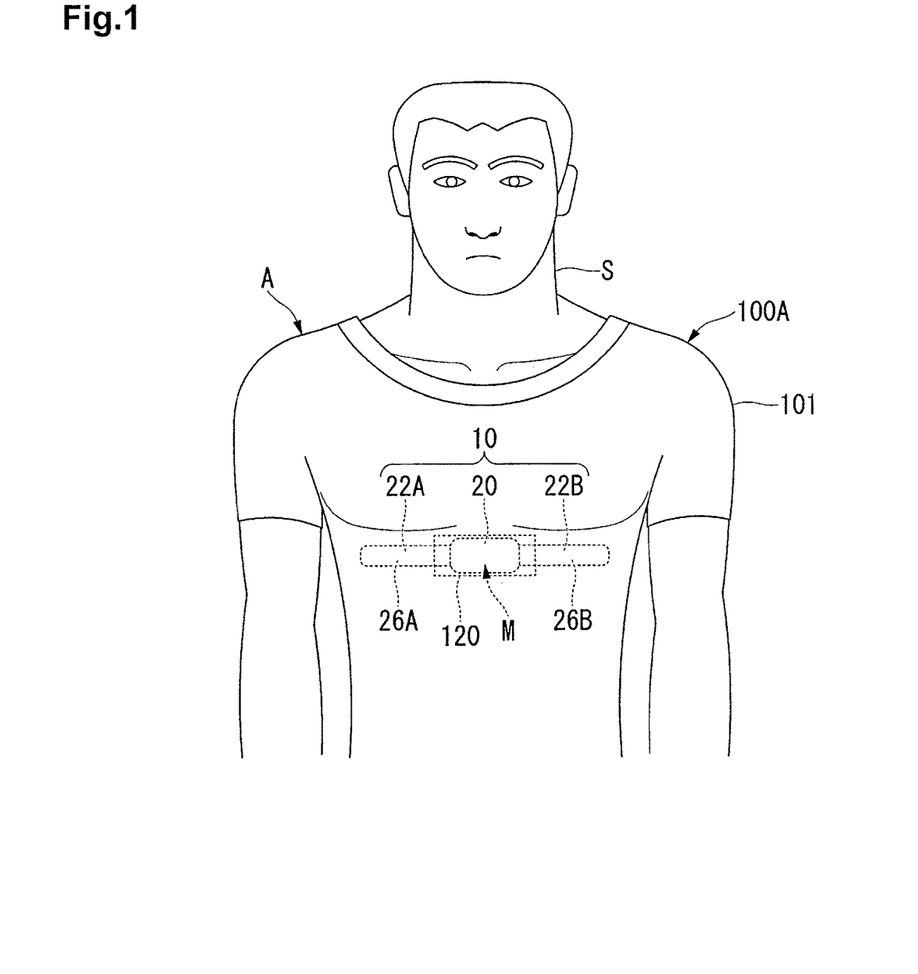
FIG. 1 is a front view showing a state where a garment according to a first embodiment of the present invention is worn by a user.
Figure 2:
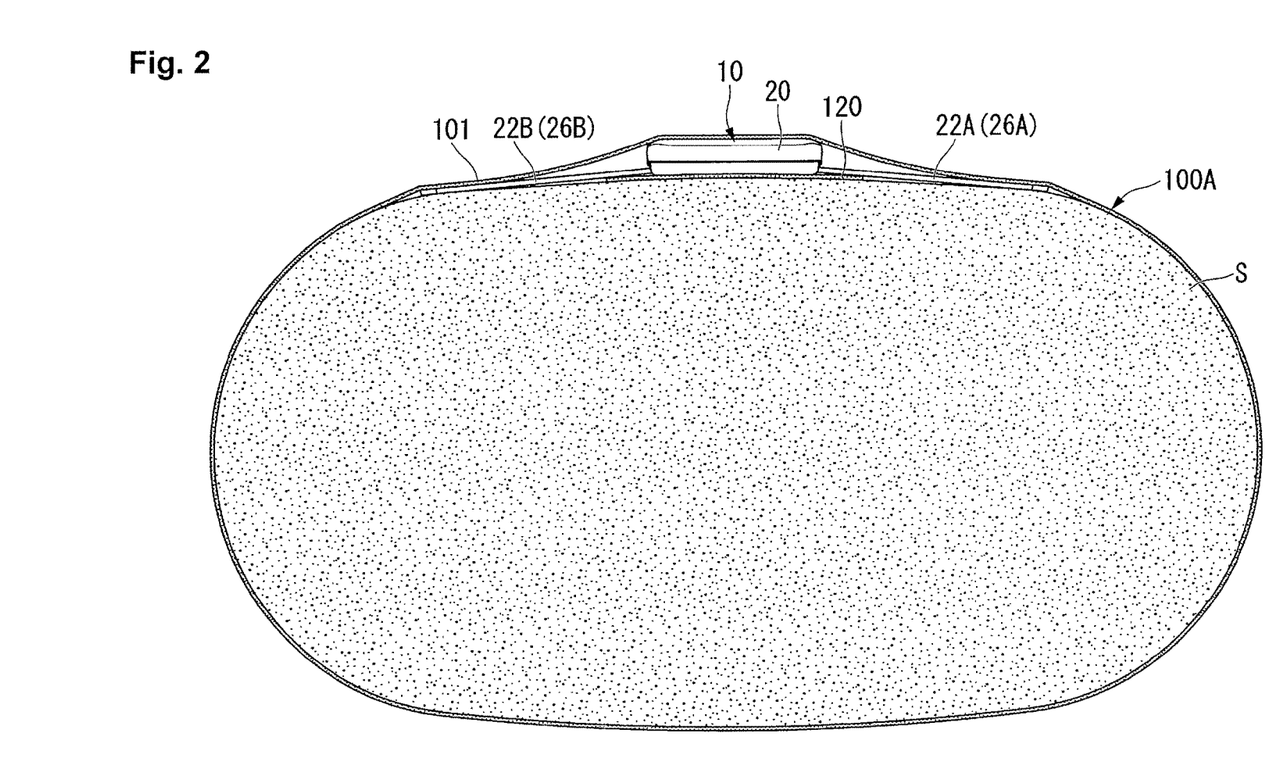
FIG. 2 is a transverse sectional view showing a state where the garment is worn by the user.
Figure 3:
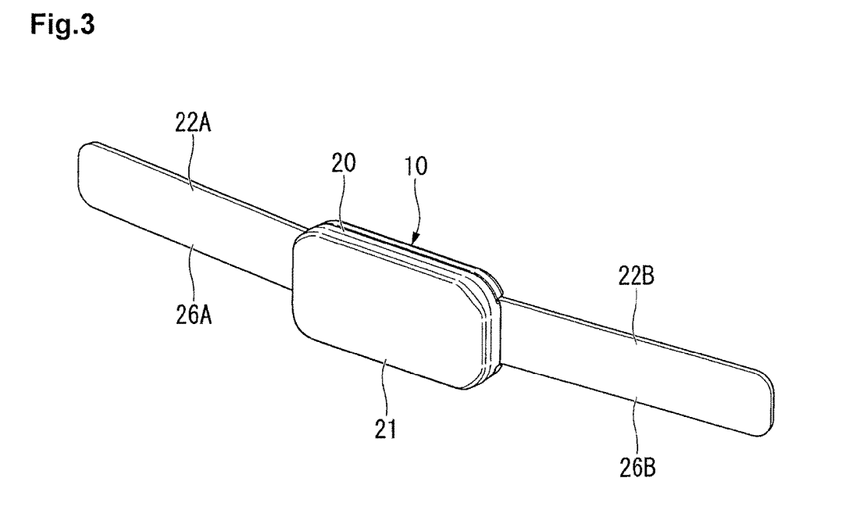
FIG. 3 is a perspective view of the heart rate measuring device.

FIG. 1 is a front view showing a state where a garment according to the present invention is worn by a user, FIG. 2 is a transverse sectional view showing a state where the garment is worn by the user and FIG. 3 is a perspective view of a heart rate measuring device.

As shown in FIG. 1, a heart rate measuring device (corresponding to a "biological information detecting device" in claims) 10 closely contacts a chest of a user S as a biological surface by being attached to a garment 100A to be worn by the user to thereby detect an electrocardiographic signal generated by heartbeats, and transmits the detected electrocardiographic signal by wireless communication.

As shown in FIG. 2, the heart rate measuring device 10 includes a device body 20 and a pair of heart rate detecting portions 22A and 22B integrally formed on both sides of the device body 20.

As shown in FIG. 3, the device body 20 includes a case 21 formed in a rectangular shape in planer view and a not-shown detection circuit substrate provided inside the case 21.

The detection circuit substrate includes a transmission circuit generating an electric signal based on a signal detected by the pair of heart rate detecting portions 22A and 22B and a wireless transmission portion (both are not shown) transmitting the electric signal generated in the transmission circuit to the outside.

The heart rate detecting portions 22A and 22B are respectively formed by band-shaped electrodes (corresponding to "electrode portions" in claims 26A and 26B which are made of conductive elastomer. As the conductive elastomer, for example, conductive silicon rubber in which carbon black is blended, conductive rubber in which carbon black is blended, conductive polyurethane rubber in which carbon black is blended and so on can be used.

The respective heart rate detecting portions 22A and 22B are arranged in both sides interposing the device body 20 therebetween. The electrodes 26A and 26B of the respective heart rate detecting portions 22A and 22B are arranged with a prescribed distance (for example, approximately 10 cm along the longitudinal direction of the device body 20 in the example of FIG. 1) for securing a potential difference between both electrodes 26A and 26B. The electrodes 26A and 26B are also electrically connected to the detection circuit substrate in the case 21 through not-shown wiring patterns. Accordingly, the signal detected by the electrodes 26A and 26B is outputted to the detection circuit substrate.

In the above heart rate measuring device 10, an electrocardiographic signal generated by heartbeats of the user S is detected by allowing the pair of electrodes 26A and 26B to contact a body surface (biological surface) of the user S. The not-shown detection circuit substrate of the device body 20 outputs the electrocardiographic signal detected by the pair of electrodes 26A and 26B to the outside by wireless communication.

Figure 4:
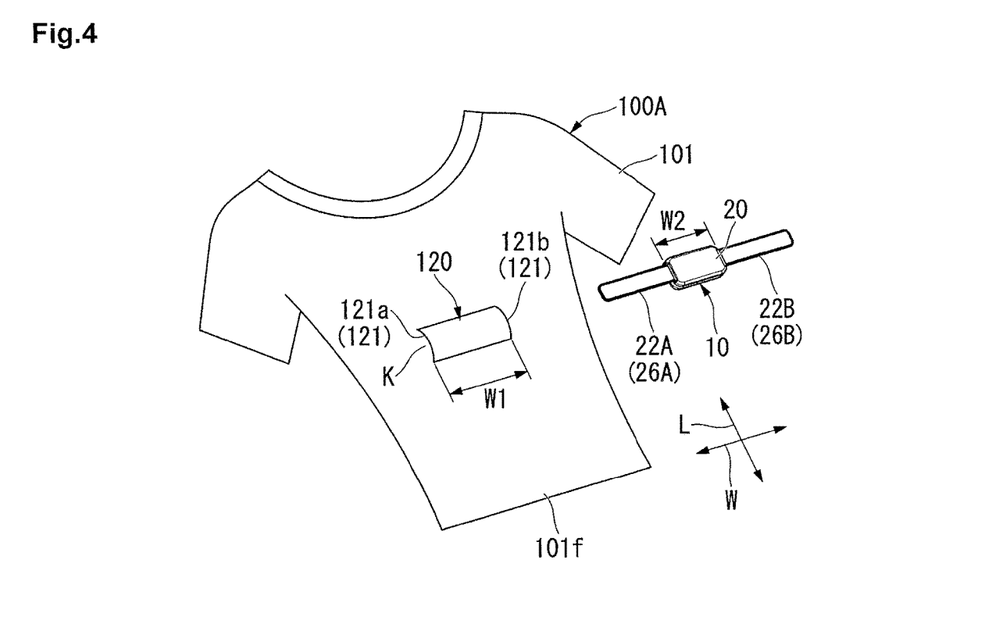
FIG. 4 is a view showing a garment in an inside-out state, which is a perspective view showing a state before the heart rate measuring device is held in a device housing portion of the garment.
Figure 5:
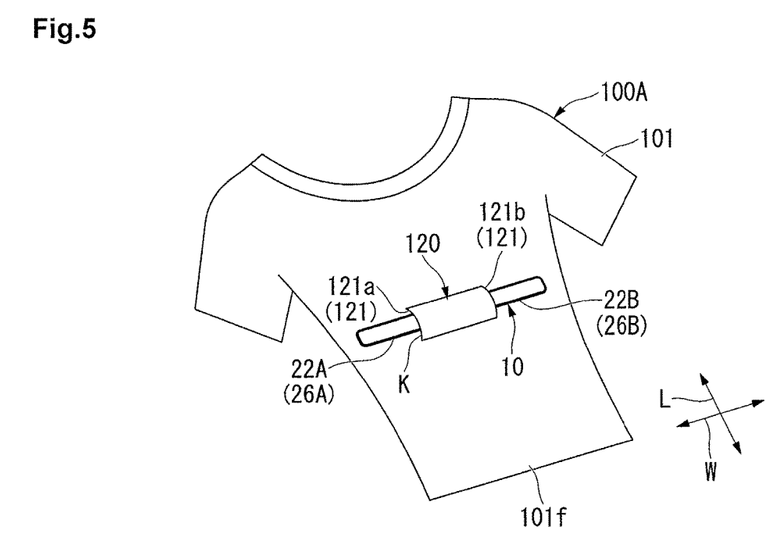
FIG. 5 is a perspective view showing a state where the heart rate measuring device is held in the device housing portion of the garment shown in FIG. 4.

FIG. 4 is a view showing a garment in an inside-out state, which is a perspective view showing a state before the heart rate measuring device is held in a device housing portion of the garment. FIG. 5 is a perspective view showing a state where the heart rate measuring device is held in the device housing portion of the garment shown in FIG. 4.

As shown in FIG. 4 and FIG. 5, the heart rate measuring device 10 is used by being attached to the garment 100A.

The garment 100A is, for example, a shirt, which includes a garment body 101 and one device housing portion 120 provided in the garment body 101 and holding the heart rate measuring device 10 so as to be attached/detached.

The garment body 101 is preferably a so-called compression wear made of a material having stretch property in a lengthwise direction L (corresponding to a "first direction" in claims) and a width direction W (corresponding to a "second direction" in claims) perpendicular to the lengthwise direction L and supporting muscles and so on by wrapping the body moderately. Accordingly, the heart rate detecting portions 22A and 22B can closely contact the surface of the body of the user S and the detection of the biological signal can be performed with high sensitivity when the heart rate measuring device 10 is housed in the device housing portion 120.

The device housing portion 120 is a cloth material having a rectangular shape in planar view and made of, for example, the same material as the garment body 101, and long side portions which are opposite to each other are sewn to a reverse surface 101$f$ side (side facing the body surface of the user S) of the garment body 101.

The device housing portion 120 is sewn to a portion positioned in the vicinity of the pit of the stomach M (refer to FIG. 1) of the user S in a state where the user S wears the garment 100A so that the long side portions correspond to the width direction W of the garment body 101. Accordingly, the device housing portion 120 defines between the device housing portion 120 itself and the garment body 101, a tubular housing space K having openings 121 (121$a$, 121$b$) opening toward both sides along the width direction W. In the heart rate measuring device 10, the device body 20 is housed inside the housing space K in a state where the heart rate detecting portions 22A and 22B are exposed from the housing space K.

Note that the material of the device housing portion 120 may be a different material from the garment body 101. Therefore, for example, materials having stretch property along plane directions typified by a rubber material, a jersey material and so on can be used.

Here, as shown in FIG. 4, a width size W1 extending along the width direction W of the device housing portion 120 is preferably ½ or more of a size W2 in the longitudinal direction of the device body 20. The width size W1 of the device housing device 120 can be larger than the size W2 of the device body 20 as long as the potential difference between both electrodes 26A and 26B is secured.

A length of the opening 121 along the lengthwise direction L of the device housing portion 120 is preferably equivalent to a size of the device body 20 along the short side direction or shorter than the size of the device body 20 along the short side direction. Accordingly, the device housing portion 120 can house the device body 20 in a stretched state. Therefore, the device body 20 is stably held in the device housing portion 120.

(Operation)

Next, a use method of the garment 100A will be explained.

When the heart rate measuring device 10 is attached to the garment 100A, the garment 100A is turned inside out to expose the device housing portion 120 to the outside (see FIG. 4).

Next, the heart rate measuring device 10 is inserted into the device housing portion 120 in a state where the heart rate measuring device 10 is positioned so that the longitudinal direction of the device body 20 corresponds to the width direction W. Specifically, the heart rate measuring device 10 is inserted into the housing space K by inserting one (left side in FIG. 4) heart rate detecting portion 22A in the heart rate detecting portions 22A and 22B of the heart rate measuring device 10 into the other opening 121$b$ (right side in FIG. 4) of the device housing portion 120.

Subsequently, the heart rate measuring device 10 is inserted into the device housing portion 120 until one heart rate detecting portion 22A in the heart rate detecting portions 22A and 22B of the heart rate measuring device 10 is exposed to the outside through one opening 121a in the device housing portion 120, and the other heart rate detecting portion 22B is exposed to the outside through the other opening 121b in the device housing portion 120. Accordingly, the device body 20 is housed in the housing space K of the device housing portion 120 in the state where the respective heart rate detecting portions 22A and 22B are exposed to the outside of the device housing portion 120.

Here, as the device housing portion 120 is made of the same material as the garment body 101, the device housing portion 120 is stretched and deformed when the heart rate measuring device 10 is inserted into the device housing portion 120. Accordingly, the heart rate measuring device 10 can be inserted into the device housing portion 120 smoothly. Also, as the device housing portion 120 houses the heart rate measuring device 10 in the stretched state, the device body 20 is housed inside the housing space K positively.

In the manner as described above, the attachment work of the heart rate measuring device 10 to the garment body 101 is completed.

Subsequently, the heart rate detecting portions 22A and 22B are exposed to the inside of the garment 100A (namely, the body surface side of the user S) by turning the garment 100A right side out. Then, when the user S wears the garment 100A in this state, the electrodes 26A and 26B of the heart rate detecting portions 22A and 22B contact the body surface of the user S, therefore, the electrocardiographic signal of the user S can be detected.

According to the embodiment, the device body 20 is held by the device housing portion 120, and the electrodes 26A and 26B are exposed toward the body surface of the user S. Accordingly, the heart rate measuring device 10 can be held in the state where the electrodes 26A and 26B contact the body surface as the user S wears the garment 100A.

As the heart rate measuring device 10 can be attached/detached to and from the device housing portion 120, the heart rate measuring device 10 can be detached from the garment body 10 when the garment body 101 is washed. Accordingly, as the garment body 101 can be washed alone, the garment body 101 can be changed freely, and the heart rate measuring device 10 (for example, electrodes 26A, 26B and the like) are not deteriorated by the washing. Furthermore, as the heart rate measuring device 10 can be held only by providing the device housing portion 120, improvement in productivity and reduction of costs can be realized. Therefore, it is possible to suppress the reduction of product lifetime, to improve productivity and to reduce costs.

As the user can attach the heart rate measuring device 10 to plural garment bodies 101 by turns, the heart rate measuring device 10 can be continuously used day by day only by preparing a plurality of garment bodies 101, which can suppress expenses for the user.

As the device housing portion 120 is formed by the material having stretch property and the device housing portion 120 houses the device body 20 in the stretched state, the device body 20 can be positively held by the stretch property of the device housing portion 120.

As the device housing portion 120 is sewn to the garment body 101 and the tubular housing space K is formed between the device housing portion 120 and the surface of the garment body 101, the device body 20 can be held by the housing space K.

Respective Embodiments

Subsequently, respective embodiments of the garment according to the present invention will be explained.

In the first embodiment, one device housing portion 120 holding the heart rate measuring device 10 so as to be attached/detached is provided in the garment body 101 of the garment 100A. On the other hand, the number, the form and so on of the device housing portion are not limited to the first embodiment and various modification may occur as shown in second to seventh respective embodiments. In respective embodiments explained below, components common to the first embodiment are denoted by the same reference numerals and signs, and explanation thereof is omitted.

Second Embodiment

Figure 6:
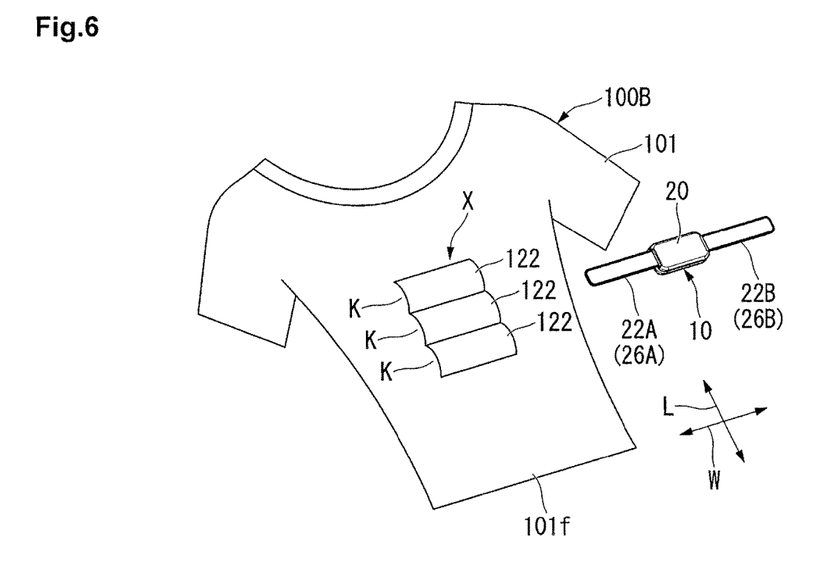
FIG. 6 is a perspective view showing a state before the heart rate measuring device is held in a device housing portion of a garment according to a second embodiment of the present invention.
Figure 7:
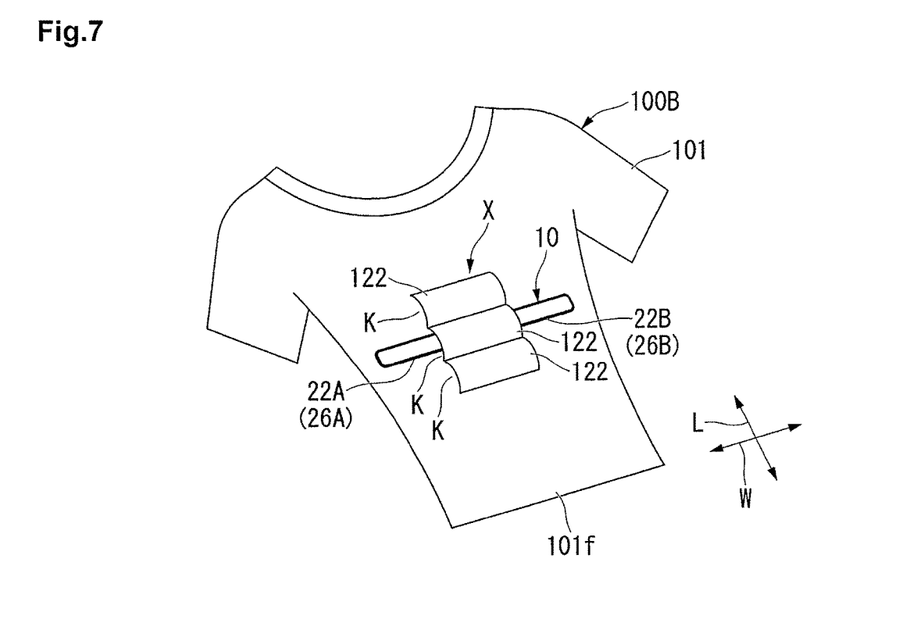
FIG. 7 is a perspective view showing a state where the heart rate measuring device is held in the device housing portion of the garment shown in FIG. 6.

FIG. 6 is a perspective view showing a state before the heart rate measuring device is held in the device housing portion of the garment according to a second embodiment of the present invention. FIG. 7 is a perspective view showing a state where the heart rate measuring device is held in the device housing portion of the garment shown in FIG. 6.

As shown in FIG. 6 and FIG. 7, a garment 100B includes the garment body 101 and device housing portions 122 provided in the garment 101 and holding the heart rate measuring device 10 so as to be attached/detached.

A plurality of (three in the embodiment) device housing portions 122 are arranged along the lengthwise direction L of the garment body 101 to thereby form a housing portion group X.

Respective device housing potions 122 may be formed by sewing a piece of cloth material to the garment body 101 with a given pitch in the lengthwise direction to thereby set portions between respective sewn portions as respective device housing portions 122, or respective device housing portions 122 may be formed by sewing cloth materials as divided device housing portions 122 to thereby set the cloth materials as respective device housing portions 122. The device body 20 can be housed in each of plural housing spaces K formed between the device housing portions 122 and the reverse surface 101f of the garment body 101.

The user S selects the device housing portion 122 suitable for the body of himself/herself from plural device housing portions 122. Then, the device body 20 is housed in the housing space K formed between the selected device housing portion 122 and the reverse surface 101f of the garment body 101.

According to the embodiment, the device housing portion 122 for holding the device body 20 can be selected from the housing portion group X. As the position of the device body 20 can be adjusted along the lengthwise direction L of the garment body 101, the device body 20 can be attached so as to be fitted to the body of the user S. As a result, the device body 20 can be attached to an appropriate position to thereby fulfill a required function. The user S can also attach the device body 20 at a position comfortable for the user S.

Third Embodiment

Figure 8:
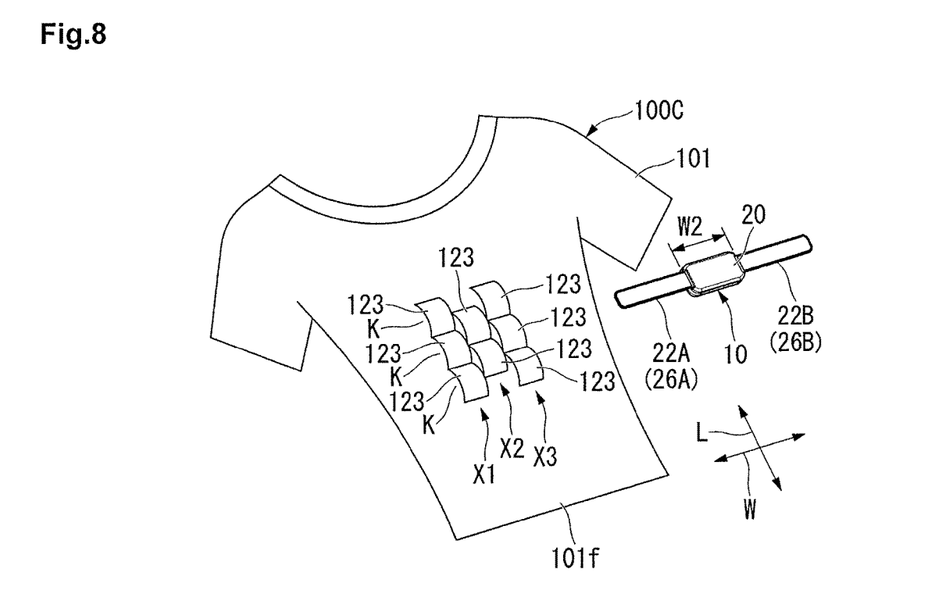
FIG. 8 is a perspective view showing a state before the heart rate measuring device is held in device housing portions of a garment according to a third embodiment of the present invention.
Figure 9:
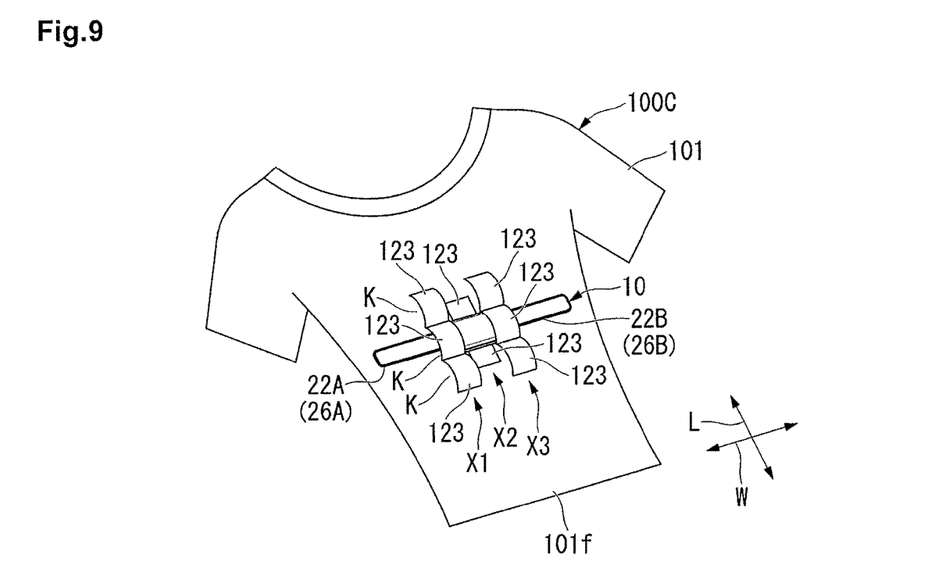
FIG. 9 is a perspective view showing a state where the heart rate measuring device is held in the device housing portions of the garment shown in FIG. 8.

FIG. 8 is a perspective view showing a state before the heart rate measuring device is held in device housing portions of a garment according to a third embodiment of the present invention. FIG. 9 is a perspective view showing a state where the heart rate measuring device is held in the device housing portions of the garment of FIG. 8.

As shown in FIG. 8 and FIG. 9, a garment 100C includes the garment body 101 and device housing portions 123 provided in the garment 101 and holding the heart rate measuring device 10 so as to be attached/detached.

In the present embodiment, a plurality of device housing portions 123 are arranged along the lengthwise direction L to thereby form a plurality of housing portion groups (a first housing portion group X1 to a third housing portion group X3), which are aligned in the width direction W of the garment body 101. Specifically, in the first housing portion group X1 and the third housing portion group X3 positioned at both sides in the width direction W, three device housing portions 123 are arranged along the lengthwise direction L. In the first housing portion group X1 and the third housing portion group X3, corresponding respective device housing portions 123 are positioned at the same height along the lengthwise direction L.

In the second housing portion group X2 positioned between the first housing portion group X1 and the third housing portion group X3, two device housing portions 123 are arranged along the lengthwise direction L. Positions of the respective device housing portions 123 in the second housing portion group X2 along the lengthwise direction differ from positions of the respective device housing portions 123 of the first housing portion group X1 and the third housing portion group X3. In the shown example, the respective device housing portions 123 of the second housing portion group X2 are positioned between the respective device housing portions 123 of the first housing portion group X1 and the third housing portion group X3.

According to the present embodiment, the device body 20 can be positively held by plural device housing portions 123 arranged in the width direction W. When device body 20 is allowed to be held in the device housing portion 123 of the second housing portion group X2 positioned between the first housing portion group X1 and the third housing portion group X3, the device body 20 can be held between device housing portions 123 in the first housing portion group X1 and the third housing portion group X3 in the lengthwise direction L. Accordingly, the device body 20 can be held in a desired portion.

Fourth Embodiment

Figure 10:
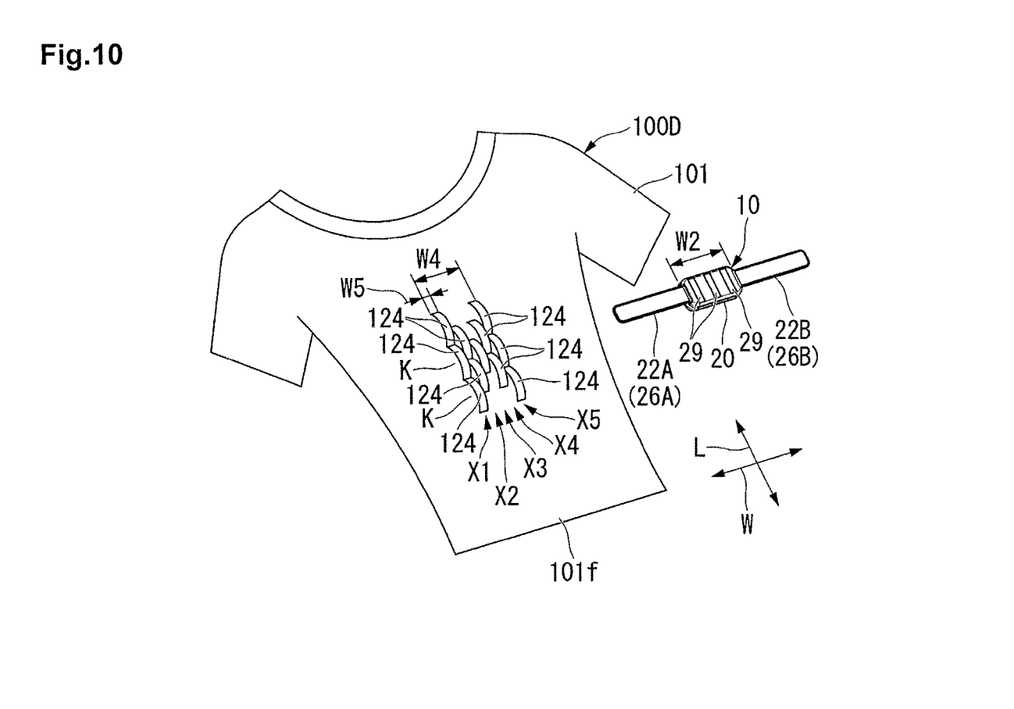
FIG. 10 is a perspective view showing a state before the heart rate measuring device is held in device housing portions of a garment according to a fourth embodiment of the present invention.
Figure 11:
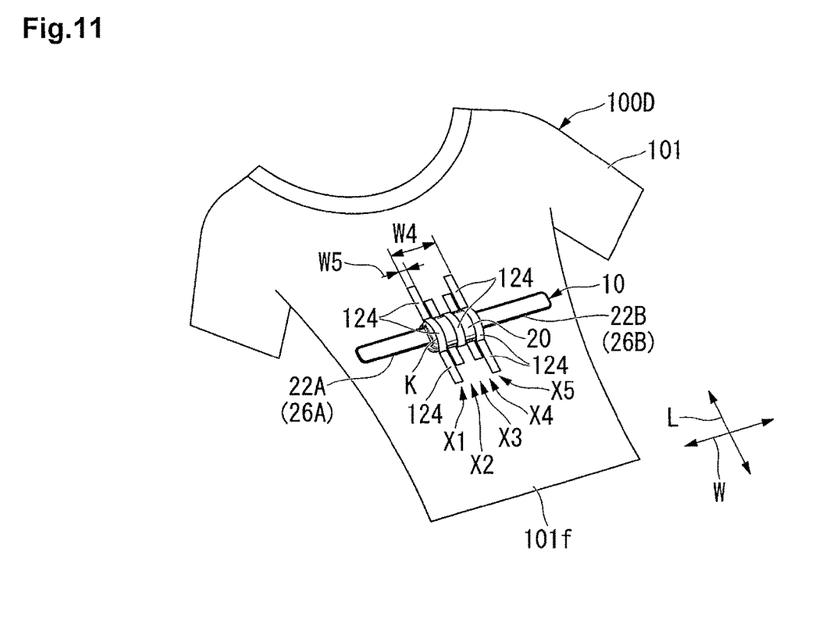
FIG. 11 is a perspective view showing a state where the heart rate measuring device is held in the device housing portions of the garment shown in FIG. 10.

FIG. 10 is a perspective view showing a state before the heart rate measuring device is held in device housing portions of a garment according to a fourth embodiment of the present invention. FIG. 11 is a perspective view showing a state where the heart rate measuring device is held in the device housing portions of the garment of FIG. 10.

As shown in FIG. 10 and FIG. 11, a garment 100D includes the garment body 101 such as a shirt and a device housing portion 124 provided in the garment body 101 and holding the heart rate measuring device 10 so as to be attached/detached.

A plural lines of device housing portions 124 are aligned in the width direction W of the garment body 101. Specifically, in a first housing portion group X1 and a fifth housing portion group X5 positioned at both sides of the width direction W in respective housing portion groups (the first housing portion group X1 to the fifth housing portion group X5), three device housing portions 124 are arranged along the lengthwise direction L. In the second housing portion group X2 and the fourth housing portion group X4 respectively positioned adjacent to the first housing group portion X1 and the fifth housing group portion X5, two device housing portions 124 are arranged along the lengthwise direction L. In the third housing portion group X3 positioned between the second housing portion group X2 and the fourth housing portion group X4, one device housing portion 124 is arranged.

Positions of the respective device housing portions 124 of the second housing portion group X2 and the fourth housing portion group X4 along the lengthwise direction differ from positions of the respective device housing portions 124 of the first housing portion group X1 and the fifth housing portion group X5. In the shown example, the respective device housing portions 124 of the second housing portion group X2 and the fourth housing portion group X4 are positioned between the respective device housing portions 124 of the first housing portion group X1 and the fifth housing portion group X5. The device housing portion 124 of the third housing portion group X3 is positioned between the respective device housing portions 124 of the second housing portion group X2 and the fourth housing portion group X4. Therefore, the device body 20 can be held at a required position in the lengthwise direction L.

A width size W4 of the first housing portion group X1 to the fifth housing portion group X5 is approximately the same as the size W2 (see FIG. 10) in the longitudinal direction of the device body 20.

Additionally, a width size W5 of the respective device housing portions 124 is narrower than the size W2 in the longitudinal direction of the device body 20 and further narrower than a width of the device housing portions 123 (see FIG. 8) of the above-described third embodiment.

Here, grooves 29 having the width equivalent to the width of the device housing portions 124 of the first housing portion group X1 to the fifth housing portion group X5 are formed in the device body 20 at a pitch equivalent to a pitch of the first housing portion group X1 to the fifth housing portion group X5.

Accordingly, as the device housing portions 124 are fitted to the grooves 29 when the device body 20 is housed inside the housing space K, the device body 20 can be positively held by the device housing portions 124.

Fifth Embodiment

Figure 12:
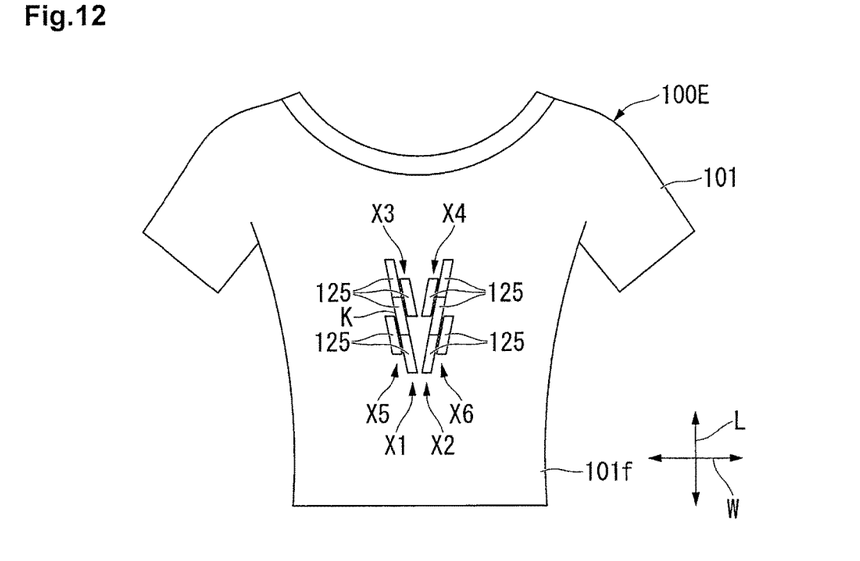
FIG. 12 is a front view showing a garment according to a fifth embodiment of the present invention.
Figure 13:
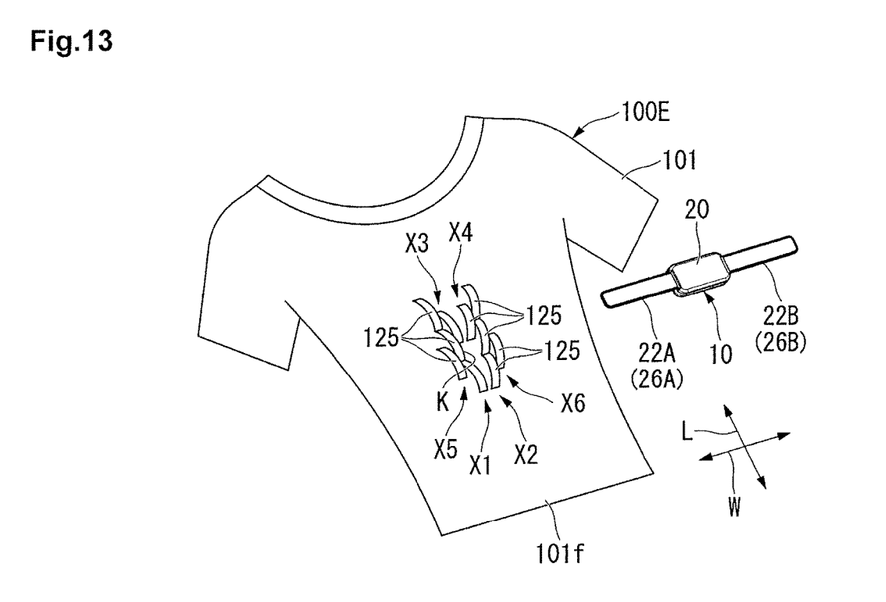
FIG. 13 is a perspective view showing a state before the heart rate measuring device is held in device housing portions of the garment shown in FIG. 12.
Figure 14:
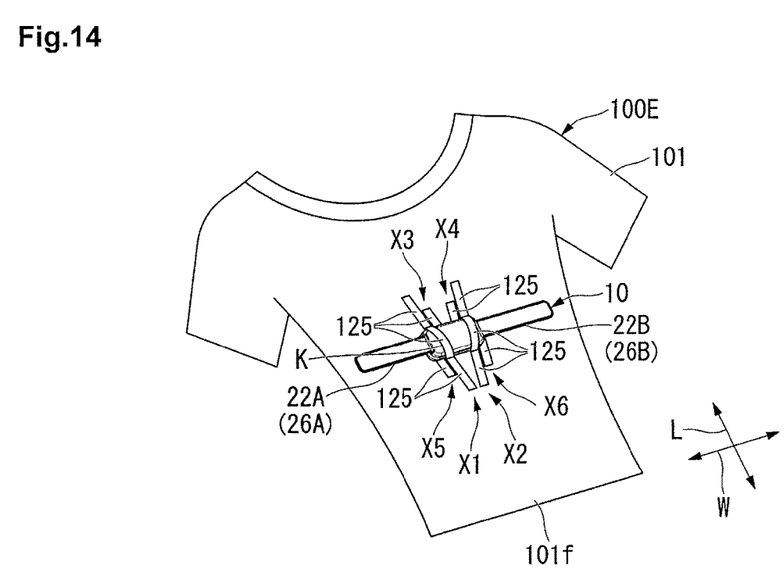
FIG. 14 is a perspective view showing a state where the heart rate measuring device is held in the device housing portions of the garment shown in FIG. 12.

FIG. 12 is a front view showing a garment according to a fifth embodiment of the present invention. FIG. 13 is a perspective view showing a state before the heart rate measuring device is held in device housing portions of a garment of FIG. 12. FIG. 14 is a perspective view showing a state where the heart rate measuring device is held in the device housing portions of the garment of FIG. 12.

As shown in FIG. 12 to FIG. 14, a garment 100E includes the garment body 101 such as a shirt and device housing portions 125 provided in the garment body 101 and holding the heart rate measuring device 10 so as to be attached/detached.

A plural lines of device housing portions 125 are aligned in the width direction W of the garment body 101. Specifically, in the first housing portion group X1 and the second housing portion group X2 arranged in a V-shape in planar view, three device housing portions 125 are arranged so as to be inclined with respect to the lengthwise direction L. The separation distance between the device housing portions 125 of the first housing portion group X1 and the device housing portions 125 of the second housing portion group X2 is gradually reduced from an upper part of the garment body 101 toward a lower part thereof.

In a third housing portion group X3 and a fourth housing portion group X4 adjacent to each other inside the first housing portion group X1 and the second housing portion group X2, one device housing portion 125 is each arranged at an upper part than an intermediate part in the lengthwise direction L of the first housing portion group X1 and the second housing portion group X2. In a fifth housing portion group X5 and a sixth housing portion group X6 adjacent to each other outside the first housing portion group X1 and the second housing portion group X2, one device housing portion 125 is each arranged at a lower part than the intermediate part in the lengthwise direction L of the first housing portion group X1 and the second housing portion group X2.

Positions of the respective device housing portions 125 of the third housing portion group X3 and the fourth housing portion group X4 along the lengthwise direction differ from positions of the respective device housing portions 125 of the first housing portion group X1 and the second housing portion group X2. In the shown example, the respective device housing portions 125 of the third housing portion group X3 and the fourth housing portion group X4 are positioned between the respective device housing portions 125 of the first housing portion group X1 and the second housing portion group X2. Also, the device housing portions 125 of the fifth housing portion group X5 and the sixth housing portion group X6 are positioned between the respective device housing portions 125 of the first housing portion group X1 and the second housing portion group X2. Therefore, the device body 20 can be held at a required position in the lengthwise direction L.

As shown in FIG. 14, the device body 20 is housed by a pair of device housing portions 125 and 125 so as to bridge between the device housing portions 125 and 125 of the first housing portion group X1 and the second housing portion group X2. Therefore, the device housing portions 125 can positively hold the device body 20.

There is a case where a lower part of the garment body 101 is deformed so as to be stretched in the width direction W, for example, when the user S who wears the garment 100E moves so as to twist the upper body. In response to this, the separation distance between the device housing portions 125 of the first housing portion group X1 and the device housing portions 125 of the second housing portion group X2 is gradually reduced from the upper part of the garment body 101 toward the lower part thereof. Accordingly, as the separation distance in the width direction W between the device housing portions 125 in the lower part is narrow, both end portions in the longitudinal direction of the device body 20 can be positively held even when the lower part of the garment body 101 is stretched in the width direction W, thereby preventing the device body 20 from falling off from the device housing portions 125.

Sixth Embodiment

Figure 15:
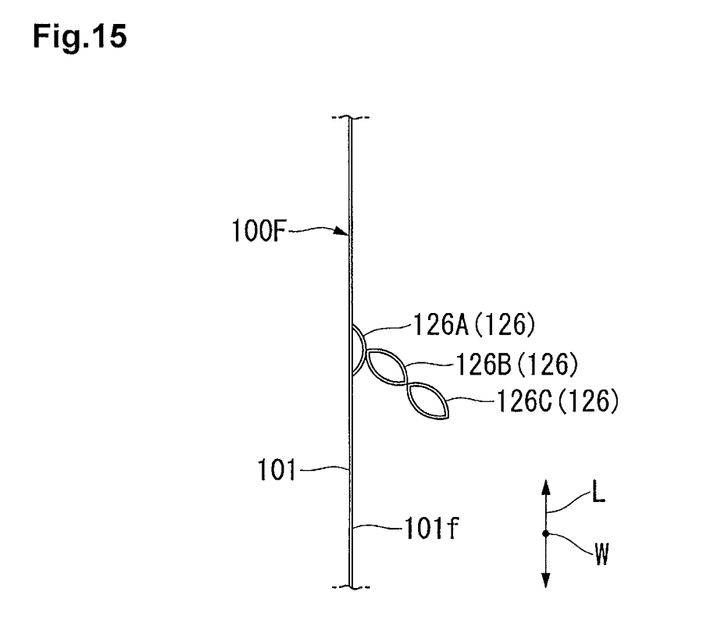
FIG. 15 is a sectional side view showing device housing portions of a garment according to a sixth embodiment of the invention.

FIG. 15 is a sectional side view showing device housing portions of a garment according to a sixth embodiment of the present invention.

As shown in FIG. 15, a garment 100F includes the garment body 101 such as a shirt and a plurality of (three in the embodiment) device housing portions 126 (126A to 126C) provided in the garment body 101 and holding the heart rate measuring device 10 so as to be attached/detached.

The three device housing portions 126A to 126C are connected in a chain shape in a sectional side view. Each of the device housing portions 126A to 126C has a tubular shape continued along the width direction W of the garment body 101. An upper edge of the device housing portion 126A at one end side in the device housing portions 126A to 126C is fixed to the reverse surface 101f of the garment body 101. The device housing portion 126C positioned in the other end side is formed to be rotatable with the device housing portion 126A positioned at one end side as an origin.

On surfaces of the device housing portions 126B and 126C and the garment body 101, not-shown hook and loop fasteners which can be engaged with each other are provided. Accordingly, the device housing portion 126B and the device housing portion 126C can be attached and detached to and from the reverse surface 101f of the garment body 101.

FIGS. 16(a) through 16(d) are sectional side views showing plural examples of holding positions of the device body by the device housing portions of the garment shown in FIG. 15.

Figure 16A:
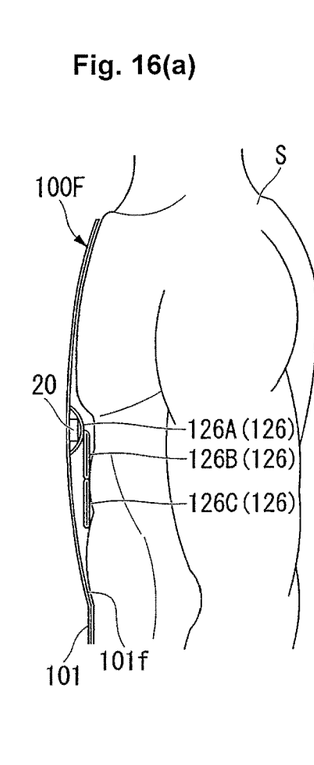
FIGS. 16(a) to 16(d) are sectional side views showing plural examples of holding positions of the device body by the device housing portions of the garment shown in FIG. 15.
Figure 16B:
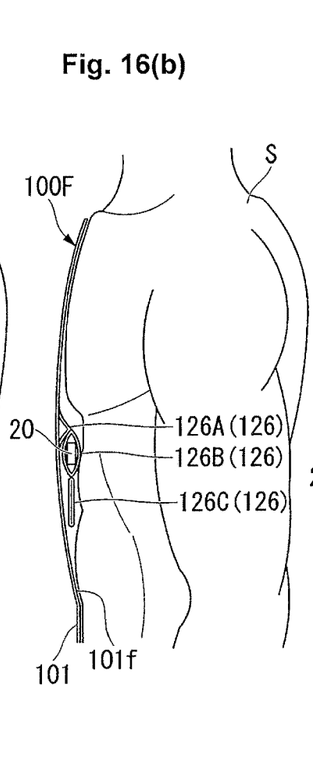
Figure 16C:
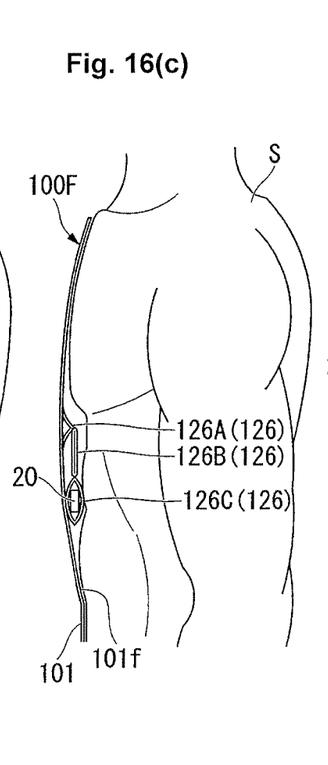
Figure 16D:
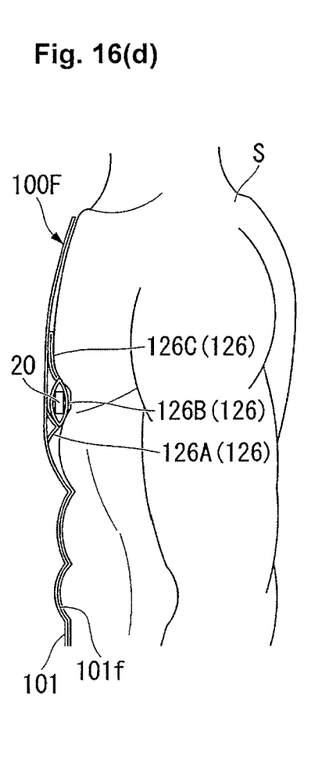

The device housing portions 126A to 126C continuously provided as described above can hold the device body 20, for example, in the device housing portion 126A at one end side as shown in FIG. 16(a). It is also possible to hold the device body 20 in the device housing portion 126B at the intermediate part in a state where the device housing portions 126A to 126C which are connected in a chain shape are allowed to hang downward from one end side as shown in FIG. 16(b). It is also possible to hold the device body 20 in the device housing portion 126C at the other end side in a state where the device housing portions 126A to 126C are allowed to hang downward from the device housing portion 126A at one end side as shown in FIG. 16(c). It is also possible to hold the device body 20 in the device housing portion 126B at the intermediate part in a state where the device housing portions 126A to 126C continuously provided are allowed to be raised upward as shown in FIG. 16(d). It is further possible to hold the device body 20 in the device holding portion 126C at the other end side in the state where the device housing portions 126A to 126C continuously provided are allowed to be raised upward, though not shown.

According to the embodiment, as the device housing portion 126C positioned at the other end side is formed to be rotatable with the device housing portion 126A positioned at one end side as an origin, the device housing portion 126B at the intermediate part and the device housing portion 126C at the other end side can be arranged freely in the lengthwise direction. Accordingly, the position of the device body 20 in the lengthwise direction can be adjusted in a wider range.

Seventh Embodiment

Figure 17:
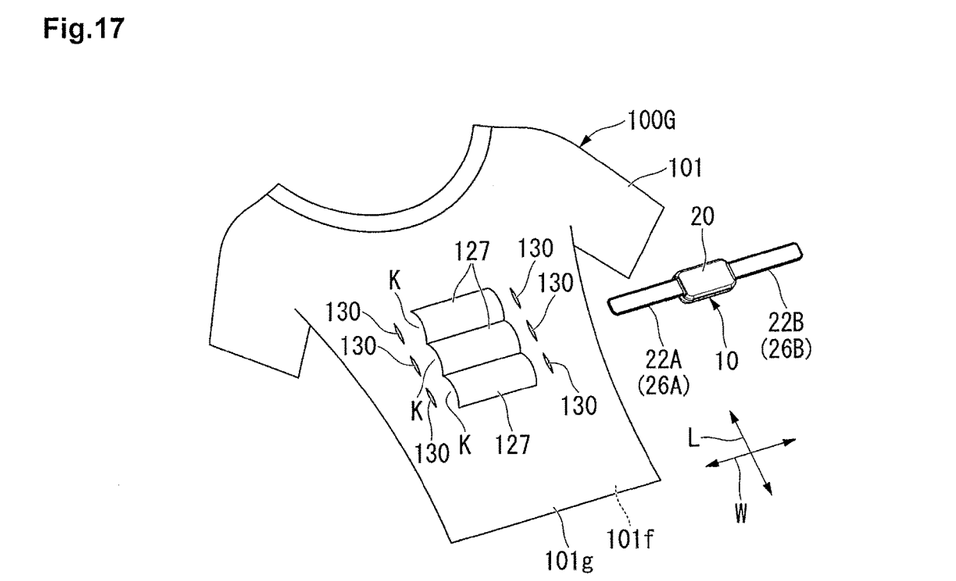
FIG. 17 is a perspective view showing a state where the heart rate measuring device is held in a device housing portion of a garment according to a seventh embodiment of the present invention.
Figure 18:
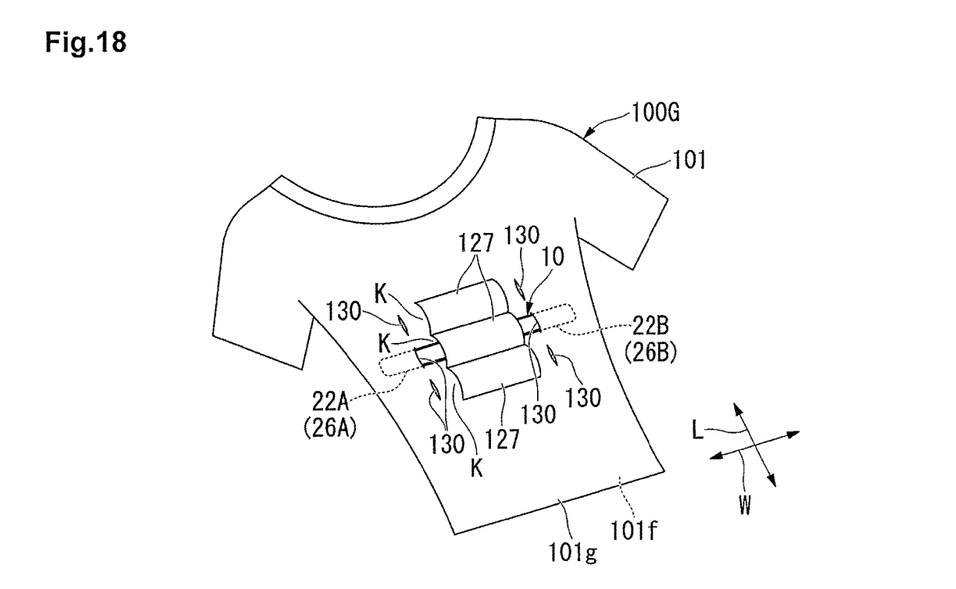
FIG. 18 is a perspective view showing a state where the heart rate measuring device is held in the device housing portion of the garment shown in FIG. 17.

FIG. 17 is a perspective view showing a state before the heart rate measuring device is held in a device housing portion of a garment according to a seventh embodiment of the present invention. FIG. 18 is a perspective view showing a state where the heart rate measuring device is held in the device housing portion of the garment in FIG. 17.

As shown in FIG. 17 and FIG. 18, a garment 100G includes the garment body 101 such as a shirt and device housing portions 127 provided in the garment body 101 and holding the heart rate measuring device 10 so as to be attached/detached.

In the embodiment, the device housing portions 127 are arranged in an obverse surface 101g side of the garment body 101. For example, three device housing portions 127 are arranged along the lengthwise direction of the garment body 101 in the same manner as the second embodiment.

Also in the garment body 101, slits 130 are respectively formed in both sides of respective device housing portions 127 in the width direction W. The slits 130 allow the electrodes 26A and 26B to pierce from the obverse surface 101g side of the garment body 101 toward the reverse surface 101f side to be drawn out to the reverse surface 101f side of the garment body 101.

According to the embodiment, even when the device housing portions 127 are arranged in the obverse surface 101g side of the garment 100G, the electrodes 26A and 26B can be drawn out to the reverse surface 101f of the garment 100G through the slits 130 to allow the electrodes 26A and 26B to contact the body surface of the user S. The slits 130 according to the embodiment can be combined with structures of other embodiments.

The present invention is not limited to the above respective embodiments explained with reference to the drawings but various modification examples can be considered within a technical scope of the invention.

For example, the outer shape of the device body 20 does not limit the structure of the device body 20 at all. For example, the outer shape of the device body 20 is not limited to the approximately rectangular shape, and other various outer shapes such as various polygonal shapes, an elliptical shape and so on can be applied.

The material of the device housing portions 120, 122 to 127 in respective embodiments may differ from the material of the garment body 101. Therefore, for example, materials having stretch property along plane directions typified by a rubber material, a jersey material and so on can be used.

Though the shirt is cited as an example of the garment body 101, the present invention is not limited to this and can be applied to all kinds of garments such as pants or a hat.

Other components in the above embodiments can be appropriately replaced with well-known components within a scope not departing from the gist of the present invention.

What is claimed is:

1. A garment for removably holding a biological information detecting device having a device body and electrode portions, comprising:
    a first set of tubular pockets arranged on an inner surface of the garment and each having a length in a width direction of the garment and a width in a height direction of the garment, the tubular pockets in the first set extending in their length direction in parallel, in the height direction of the garment, to each other,
    wherein each of the tubular pockets in the first set is sized, in its width direction, to tightly hold the biological information detecting device inside thereof and sized, in its length direction, to expose the electrode portions outside thereof so that the electrode portions are in direct contact with a biological surface side; and
    wherein the first set of tubular pockets are connected in series in the height direction of the garment, and only the tubular pocket located at one end of the series is fixed to the inner surface of the garment.

2. The garment according to claim 1, wherein the tubular pockets in the first set are each made of a stretchy material and each sized, in its width direction, smaller than a width of the biological information detecting device so that the tubular pockets in the first set are each stretchable to tightly hold the biological information detecting device inside thereof.

* * * * *